United States Patent [19]

Diamantopoulos et al.

[11] Patent Number: 4,930,504

[45] Date of Patent: Jun. 5, 1990

[54] DEVICE FOR BIOSTIMULATION OF TISSUE AND METHOD FOR TREATMENT OF TISSUE

[76] Inventors: Costas A. Diamantopoulos, 31 Alexandra Mansion, 333 Kings Road, London, SW3 5ET; Alex P. Alexandrou, 48 Woodland Gardens, London, N10 3UA, both of United Kingdom

[21] Appl. No.: 120,565

[22] Filed: Nov. 13, 1987

[51] Int. Cl.$^5$ ............................................. A61N 5/00
[52] U.S. Cl. .............................. 128/395; 250/494.1; 250/495.1; 250/504 H; 606/3; 606/13
[58] Field of Search ............ 128/395, 396, 397, 303.1, 128/362; 250/494.1, 495.1, 504 H

[56] References Cited

U.S. PATENT DOCUMENTS

| | | | |
|---|---|---|---|
| 2,072,205 | 3/1937 | Halpern | 250/494.1 |
| 3,014,156 | 12/1961 | Osterhammel et al. | 315/224 |
| 3,516,411 | 6/1970 | Adler | 128/404 |
| 3,648,706 | 3/1972 | Holzer | 250/494.1 |
| 3,785,383 | 1/1974 | Dotto | 128/395 |
| 3,818,914 | 6/1974 | Bender | 250/494.1 |
| 4,232,325 | 11/1980 | Skovajsa | 128/395 |
| 4,266,548 | 5/1981 | Davi | 128/303.1 |
| 4,408,602 | 10/1983 | Nakajima | 128/303.1 |
| 4,462,412 | 7/1984 | Turner | 128/804 |
| 4,469,098 | 9/1984 | Davi | 128/303.1 |
| 4,535,784 | 8/1985 | Rohlicek et al. | 128/735 |
| 4,553,546 | 11/1985 | Javelle | 128/395 |
| 4,558,700 | 12/1985 | Mutzhas | 128/395 |
| 4,573,465 | 3/1986 | Sugiyama et al. | 128/303.1 |
| 4,580,557 | 4/1986 | Hertzmann | 128/303.1 |
| 4,614,190 | 9/1986 | Seanco et al. | 128/395 |
| 4,625,728 | 12/1986 | Schonberg | 128/395 |
| 4,638,813 | 1/1987 | Turner | 128/804 |
| 4,646,743 | 3/1987 | Parris | 128/396 |
| 4,671,285 | 6/1987 | Walker | 128/395 |
| 4,672,969 | 6/1987 | Dew | 128/397 |

FOREIGN PATENT DOCUMENTS

| | | | |
|---|---|---|---|
| 2809007 | 9/1979 | Fed. Rep. of Germany. | |
| 2371935 | 11/1976 | France. | |
| 2571264 | 4/1986 | France | 128/395 |
| 2589067 | 4/1987 | France | 128/395 |
| 2598608 | 11/1987 | France | 128/303.1 |
| 0157667 | 12/1982 | German Democratic Rep. | 128/395 |

OTHER PUBLICATIONS

Parrish, "Photomedicine: Potentials for Lasers. An Overview" in *Lasers in Photomedicine and Photobiology*, ed. Pratesi, (Springer 1980), pp. 2–22.
Smith, "Common Misconceptions about Light" in *Lasers in Photomedicine and Photobiology*, ed. Pratesi, (Springer, 1980), pp. 23–25.
Jori, "The Molecular Biology of Photodynamic Action" in *Lasers in Photomedicine and Photobiology*, ed. Pratesi, (Springer, 1980), pp. 58–66.
Neuromed, Inc. Brochure: Omniprobe IR.
Space Laser s.r.l., Brochure: Space Laser.
Nor-Art Medical AB, Brochure: Space Laser.
Omega Universal Technologies, Brochure: Biotherapy 3.

*Primary Examiner*—Edward M. Coven
*Assistant Examiner*—Jessica J. Harrison
*Attorney, Agent, or Firm*—Dorsey & Whitney

[57] ABSTRACT

A device for biostimulation of tissue is disclosed comprising an array of substantially monochromatic radiation sources of a plurality of wavelengths, preferably of at least three different wavelengths. The radiation sources are arranged within the array such that radiation of at least two different wavelengths passes directly or indirectly through a single point located within the treated tissue. The radiation sources are preferably laser diodes, superluminous diodes or similar light-emitting diodes that, while low-power radiation sources, can provide significant energy densities to a treatment area. A method of treatment of tissue comprising exposing the treated tissue to the above-described device is also disclosed. The device for biostimulation of tissue may be included within a system with a control panel, a power source, variable pulse frequency, variable pulse duration, a timer for timing the period of treatment, a device for measuring the conductivity of the treated tissue, a device for measuring the optical power emitted by the radiation sources and/or a device for detecting emissions from the radiation sources.

43 Claims, 5 Drawing Sheets

DEVICE FOR BIOSTIMULATION OF TISSUE AND METHOD FOR TREATMENT OF TISSUE

FIELD OF THE INVENTION

This invention relates to a new and improved device, method and system for biostimulation of tissue with low-power radiation, preferably substantially monochromatic radiation, having a plurality of wavelengths and having significant power densities over a treatment area.

BACKGROUND OF THE INVENTION

For many years, high-powered, highly focused lasers have been widely used to cut and destroy tissue in many surgical techniques. More recently, low-powered lasers, less sharply focused, which do not sever or destroy tissue have been found or are thought to effect numerous metabolic processes, including cell division, cyclic-AMP metabolism, oxidative phosphorylation, hemoglobin, collagen and other protein synthesis, leukocyte activity, tumor growth, production of macrophage cells and wound healing. See, for example, Karu and Letokhov "Biological Action of Low-Intensity Monochromatic Light in the Visible Range" in *Laser Photobiology and Photomedicine*, ed. Martellucci, p. 57-66 (Plenum Press 1985); Passarella, et al., "Certain Aspects of Helium-Neon Laser Irradiation on Biological Systems in Vitro" in *Laser Photobiology and Photomedicine*, ed. Martellucci p. 67-74 (Plenum Press 1985); see generally, Parrish, "Photomedicine: Potentials for Lasers. An Overview," in *Lasers in Photomedicine and Photobiology*, ed. Pratesi, p. 2-22 (Springer 1980); Giese, "Basic Photobiology and Open Problems" in *Lasers in Photomedicine and Photobiology*, ed. Pratessi, p. 26-39 (Springer 1980); Jori, "The Molecular Biology of Photodynamic Action" in *Lasers in Photomedicine and Photobiology*, ed. Pratesi, p. 58-66 (Springer 1980). Although the precise mechanism for these effects is not fully understood, it is believed to be tied to the activity of specific wavelengths of radiation in or near the range of visible light. Infrared laser radiation has been shown to increase ATP concentration and ATPase activity in living tissues. Bolognani, et al., "Effects of GaAs Pulsed Lasers on ATP Concentration and ATPase Activity In Vitro and In Vivo", *International Cong. on Lasers in Medicine and Surgery*, p. 47 (1985).

Radiation sources operating in or near the range of visible light, including lasers, emit photons which may interact with biological molecules to produce photochemical reactions and subsequent biologic effects. Photochemical and photobiological events at the atomic level depend upon the wavelength of radiation used to cause such events and occur without regard to the source of photons. However, the molecular effects, kinetics and products can be quantitatively and qualitatively altered one or more by other properties of radiation sources, e.g., monochromaticity, coherence and high power and energy density.

Most forms of photoexcitation are "quantum specific," i.e., excitation will only occur if a bundle of energy of a precise quantity is present to excite a given molecule or part of a molecule. A photon has energy E according to the formula:

$$E = h \times f = \frac{h \times c}{\text{wavelength}}$$

where f is frequency, h is Planck's constant and c is the speed of light. If a photon having a quantum of too little or too much energy is directed at a target molecule, it may not be absorbed; the photon must be of an exact energy to have an effect.

Only radiation which is absorbed has photochemical effects. X-rays, gamma rays and other absorbed high-energy photons affect human tissues by relatively indiscriminate ionization of molecules. The ionized molecules are highly reactive and covalent bonds may be broken or formed. Infrared photons excite specific vibrational or rotational modes in specific target molecules. The quantum of energy required to produce vibrational or rotational excitation is dependant on the character (e.g., double bond vs. ring structure) and location (e.g., near an electrophilic group vs. near a nucleophilic group) of the molecule. While it is believed that infrared photons may affect specific biological processes or transformations, the most significant biological effect of these wavelengths is probably the heating caused by dissipation of the vibrational and rotational energy, which can significantly affect biological reactions in the vicinity of the dissipating molecule. The energy of photons in the ultraviolet and visible wavelengths causes electronic excitation of specific chromophores (i.e., molecules that absorb a photon of a given wavelength and use the energy to cause transition of an electron to a higher energy state). The decay of these stimulated molecules can then lead to specific reactions, including emission of a new photon, transfer of an electron or dissipation of heat.

In the past it has been difficult, however, to expose more than the first few layers of human skin or tissue to visible (400-700 nm) and ultraviolet (200-400 nm) radiation. Pigments and other molecules in the outer layers of skin are known to absorb the majority of visible and ultraviolet radiation, as shown in FIGS. 1-3. Table 1 summarizes the approximate penetration of various wavelengths of radiation into the skin.

TABLE 1

Approximate Depth of Penetration of Optical Radiation in Fair Caucasian Skin to a Value of 1/e (37%) of the Incident Energy Density

| Wavelength, nm | Depth, nm |
|---|---|
| 250 | 2 |
| 280 | 1.5 |
| 300 | 6 |
| 350 | 60 |
| 400 | 90 |
| 450 | 150 |
| 500 | 230 |
| 600 | 550 |
| 700 | 750 |
| 800 | 1200 |
| 1000 | 1600 |
| 1200 | 2200 |

As shown in FIG. 3, no ultraviolet radiation and approximately only 5% of most visible radiation penetrates to the subcutaneous layer of the skin. As a result, applying visible and ultraviolet radiation to the skin has little or no effect upon target molecules in lower layers that would become stimulated if exposed to those wavelengths of radiation.

While higher powered radiation sources can deliver greater energy to deeper layers, it is undesirable to directly expose tissue to large amounts of ultraviolet radiation due to the adverse effects of such radiation upon some molecules and cellular functions, e.g., DNA can be "mutated" by ultraviolet radiation.

It would therefore be desirable to provide a safe device and method for biostimulation of tissue that will stimulate biological processes affected by visible red and infrared radiation and also stimulate biological processes in lower layers of tissue that are affected by ultraviolet and visible radiation and would normally be inaccessible to radiation applied to the surface of the tissue because of the absorption of visible and ultraviolet radiation by skin pigments and other molecules.

SUMMARY OF THE INVENTION

A device for biostimulation of tissue is disclosed comprising an array of substantially monochromatic radiation sources of high power density and a plurality of wavelengths, preferably of at least three different wavelengths. The radiation sources are arranged within the array such that radiation of at least two different wavelengths passes directly or indirectly through a single point located within the treatment target tissue. The radiation sources are preferably laser diodes, superluminous diodes or similar light-emitting diodes. A method of treatment of tissue comprising exposing the treated tissue to such a device is also disclosed. The device for biostimulation of tissue may be included within a system with a control panel, a power source, means for varying radiation pulse frequency, means for varying radiation pulse duration, means for timing the period of treatment, means for measuring the conductivity of the treatment target tissue, means for measuring the optical power emitted by the radiation sources and/or means for detecting emissions from the radiation sources.

It is an object of the present invention to provide a device and method for low power radiation for biostimulation of tissue that can deliver higher energy densities and a greater number of potentially biostimulative photons to deeper tissue layers.

It is another object of the invention to provide a device and method for biostimulation of tissue with multiple wavelengths of radiation.

It is a further object of the invention to provide a device and method for biostimulation of tissue utilizing semiconductor laser, superluminous or light emitting diodes as sources for low-power radiation in the infrared, visible and/or ultraviolet frequency ranges.

DETAILED DESCRIPTION OF THE INVENTION

A. System Overview

Figure 4:
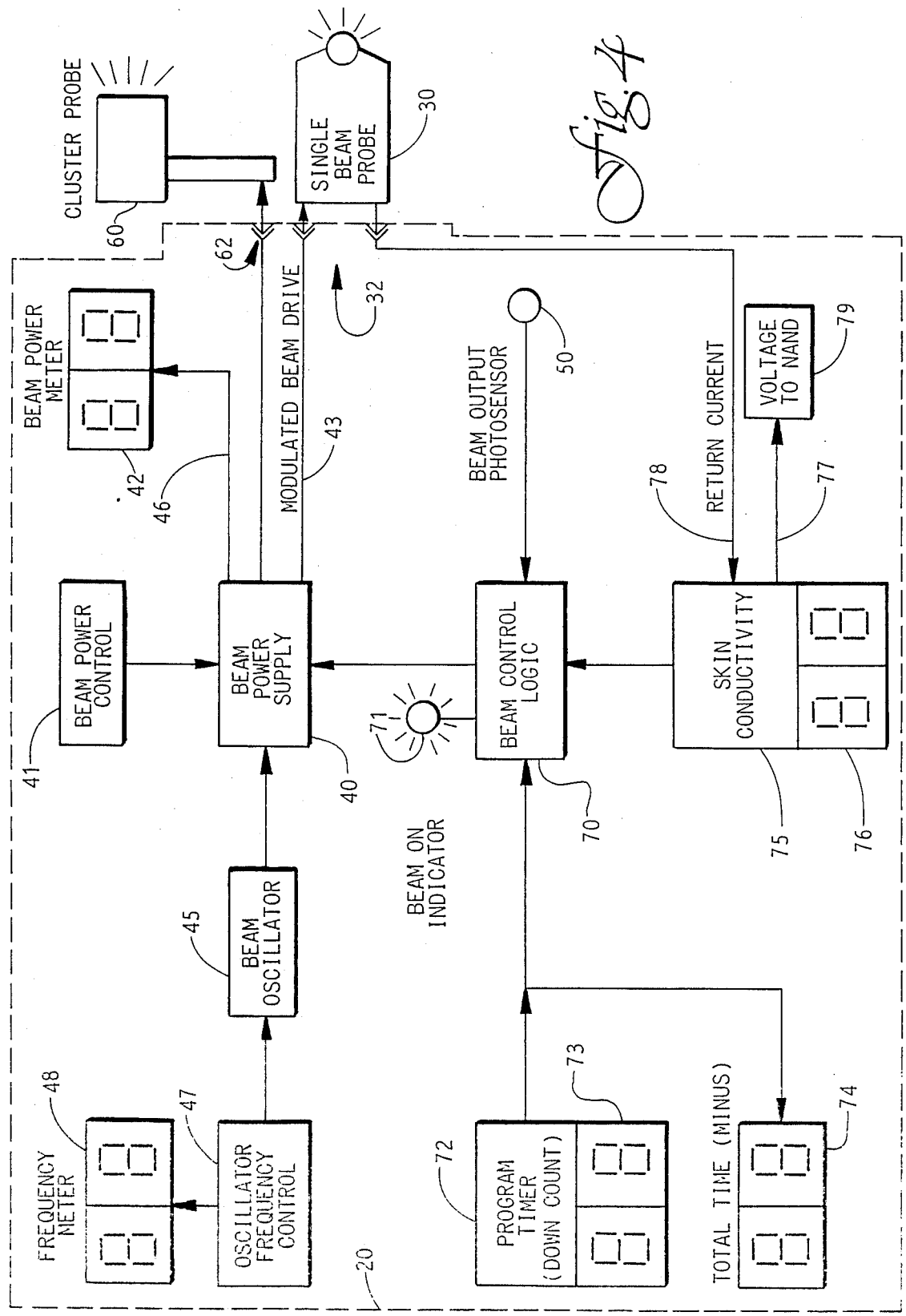
FIG. 4 is a function block diagram of the device and system of the present invention.

The block diagram of FIG. 4 shows the overall structure of the device and system of the present invention. A control unit 20 contains both controls and displays to read out control settings and measured values. To this control unit 20 a single beam probe 30 and a cluster probe 60 may be connected at plug-in connections 32 and 62, respectively. Central to the control unit 20 are a beam power supply 40 and, connected thereto, a beam control logic unit 70. The beam power supply has two output lines 43 and 46. Output line 46 leads to plug-in connection 62 for the cluster probe 60. Output line 43 leads to plug-in connection 32 for single beam probe 30.

Beam power control 41 is connected to beam power supply 40 to permit setting of the beam power level. Beam power meter 42 is connected to the beam power supply 40 to show the power level being delivered.

To provide radiation beams modulated in pulses of various frequencies, a beam oscillator 45 is connected to the beam power supply 40. The beam oscillator 45 is controlled by an oscillator frequency control 47 connected to the beam oscillator 45. A frequency meter 48 connected to the oscillator frequency control 47 provides display of the selected beam modulation frequency. If pulse duration modulation is desired as a further form of modulation, this can be accomplished by additional refinements of the beam oscillator 45 and its corresponding oscillator frequency control 47.

The beam control logic unit 70 is, as previously noted, connected to the beam power supply 40. An indicator light 71 associated with the unit shows when the beam power is on. This is useful, because the beam wavelengths being used may not be visible and treatment time, as well as power, is an important variable ($E = P \times T$). As a further check that the unit is functioning, the invention provides a beam output photosensor 50 connected to the beam control logic unit 70 (described below). This photosensor 50 is sensitive to the frequencies of radiation produced by the unit and provides a signal when it receives radiation. To aid control of treatment time, a down-counting program timer 72 with a display 73 that follows the down count is connected to the beam control logic unit 70. A further display 75, also connected to the beam control logic unit 70, provides a display of total beam on-time (in minutes).

For some uses of the invention, it is desirable to locate body points of high skin conductivity. (These usually correspond to pain trigger points of inflammatory areas, as increased temperatures will raise skin conductivity.) The present invention does this with a skin conductivity measuring module 75 connected to beam control logic unit 70, with associated display 76. This module 75 delivers a small current (microamps) via a lead 77 connected to an electrode 79 held in the hand of a patient. The single beam probe 30 is used to form a return path from a selected skin location, utilizing lead 78 as a return current path (from plug-in connection 32) to the skin conductivity measuring module 75. If desired, the skin conductivity measurement can be used as a trigger for the beam control logic unit 70; that is, the beam control logic unit 70 can be set to enable a beam only when a preselected skin conductivity level is present. When this level is chosen to be very low, the beam is enabled whenever the return path probe is in contact with a skin area to be treated.

The present invention utilizes, as noted above, radiation in or near the infrared spectrum (above 700 nm), the visible light spectrum (400-700 nm) and the ultraviolet spectrum (200-400 nm). For convenience in the following, the radiation comprising the beams produced by the present invention may be referred to as "light", although it may be in the visible or ultraviolet spectra or in other nearby spectra.

The single beam probe 30 of the present invention is shaped like a fat pencil (FIG. 4). It emits radiation of a single frequency and is therefore of limited interest in connection with the present invention. The gravamen of the invention is used of multiple radiation sources of multiple frequencies. This radiation is emitted by the multiple radiation sources contained in cluster probes 60 used with the present invention.

Figure 5:
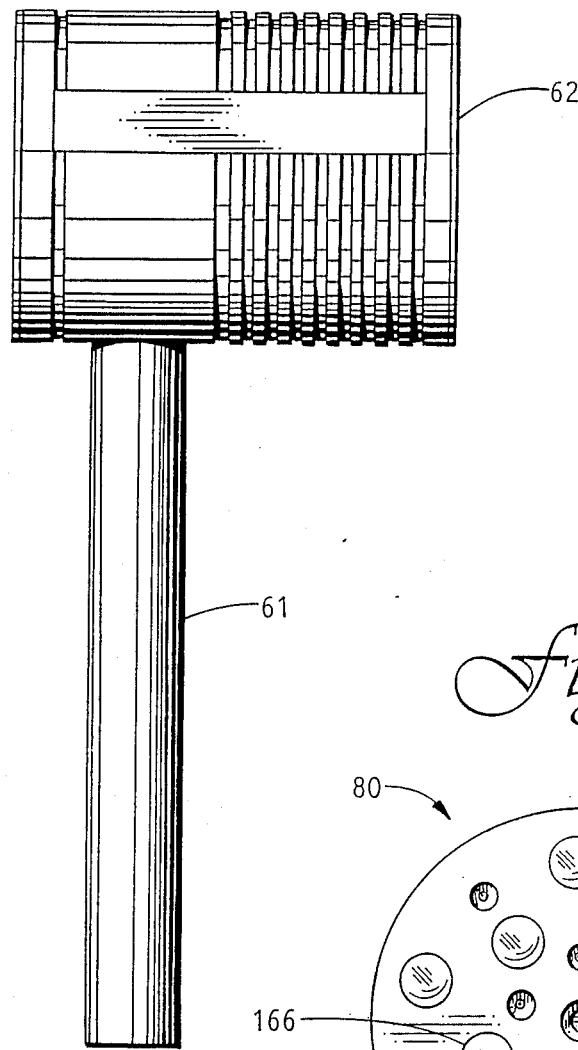
FIG. 5 is a side view of a cluster probe or radiation source array used in the present invention.
Figure 6:
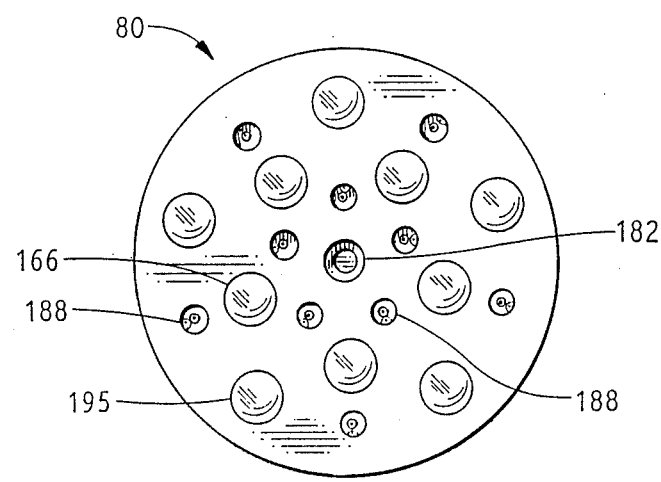
FIG. 6 is a plan view of a radiation source array used in the present invention.
Figure 7:
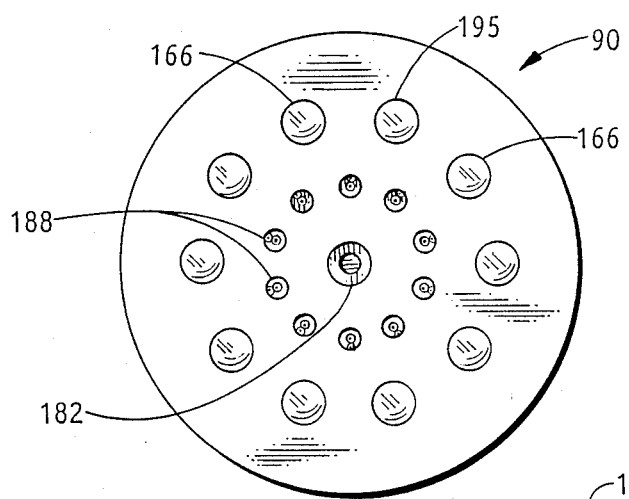
FIG. 7 is a plan view of another radiation source array comprising an alternative embodiment of the present invention.
Figure 8:
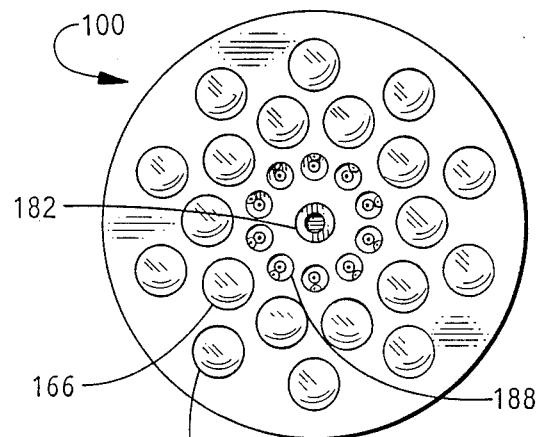
FIG. 8 is a plan view of another radiation source array comprising an alternative embodiment of the present invention.

FIG. 5 shows a side view of a cluster probe 60, having a thin cylindrical handle 61 and a thicker cylindrical head 62. FIGS. 6 through 8 show three patterns of radiation sources that can be contained within the cylindrical head 62. The radiation is emitted from a plane very near one end-face of the cylinder 62. FIGS. 6-8 show head-on views of several end-faces. As will be described below, the end-faces involve various configurations of radiation sources. Each of these configurations provides a different mix of radiation source frequencies and a somewhat different geometric configuration. These configurations accordingly produce different "mixtures" of radiation frequencies in the target tissue and different power densities.

The sources of light or radiation in each of the cluster probes 60 in FIGS. 6-8, showing particular forms of radiation arrays, are semiconductor light emitting devices, e.g., light emitting diodes (LED's). Two particular types of LED's have been found most useful for purposes of the present invention: laser diodes and superluminous diodes. Laser diodes produce a beam of light or radiation that is essentially monochromatic, is sharply collimated and is coherent. That is, they produce light almost exclusively at one frequency (unless they are multi-mode type lasers) and the light beam has a small angle of divergence. Superluminous diodes are also used. These are similar but lack the coherence and the sharply monochromatic characteristics of laser diodes; yet they produce highly directional light that is also limited in its frequency range.

A number of commercially available semiconductor laser diodes exist. Typical of these are those described in "Optoelectronic Devices Data Book" published by Hitachi, Ltd. (September, 1984).

It has been found, however, that semiconductor laser diodes having somewhat higher power outputs and narrower beam divergence and spectral widths than the most widely manufactured components are also available and may enhance the advantages of the present invention. Not all frequencies are available in the range from ultraviolet through visible to infrared radiation. But enough are available that some selection among frequencies can be made. Among low power lasers suitable for the present invention, the laser power rating (continuous power) of individual diodes is generally in the range from 5-500 milliwatts (mW). Laser diodes are available with continuous wave emission capability and as devices that must be pulsed. The following laser diode specifications have been found useful for the present invention:

1. Double Heterostructure Continuous Wave Laser Diode GaAlAs
   Wavelength: 750, 780, 800, 810, 820, 830, 850 nm
   Peak Power Output: 5 mW-500 mW (Class 3B)
   Beam Divergence: 60 parallel, 12° perpendicular (typical, variable according to manufacturing method)
   Polarisation: Linear 90-100%
   spectral Width: 0.02 mm-1.0 mm
2. Single Heterostructure Pulsed Laser Diode GaAs
   Wavelength: 904 nm
   Peak Power Output: 70W
   Avg. Power: 0.15-15 mW (frequency dependent)
   Max. Pulse Duration: 200 microsecs.
   Beam Divergence: 6°-15° parallel, 15°-30° perpendicular
   Spectral Width: less than 3.5 mm
3. Double Heterostructure Pulsed Laser Diode GaAs/GaAlAs
   Wavelength: 850-904 nm
   Peak Power: 325 mW
   Average Power: 40-80 mW
   Faxed Duty Factor (Tw×Fn): 15%; f=300 KHz, Tw=500 microsecs.
   Beam Divergence: 6°-15° parallel, 15°-30° perpendicular
   Spectral Width: 2-3 mm As best seen in FIG. 6, the preferred embodiment of the cluster probe 60 of the present invention comprises an array 80 of five 660 nm superluminous diodes 166, one 820 nm laser diode 182, ten 880 nm superluminous or laser diodes 188 and five 950 nm superluminous diodes 195. The diodes are arranged in a planar array such that the 820 nm diode 182 is positioned in the center of the array, five of the ten 880 nm diodes 188 are evenly positioned about the circumference of a circle of about 950 mm radius from the center of the array, the five 660 nm diodes 166 are evenly positioned about the circumference of a circle of about 18 mm radius from the center of the array such that a radial line from the center of the array to each 660 nm diode 166 bisects the arc between two of the innermost 880 nm diodes 188, the 950 nm diodes 195 are evenly positioned about the circumference of a circle of about 27 mm radius from the center of the array such that a radial line from the center of the array to each 950 nm diode 195 passes through the center of one of the innermost 880 nm diodes 188, and the remaining five 880 nm diodes 188 are evenly positioned about the circumference of a circle of about 27 mm radius from the center of the array such that a radial line from the center of the array to each outer 880 nm diode 188 passes through the center of one of the 660 nm diodes 166.

In an alternative embodiment shown in FIG. 7, the 820 nm diode, 182 is positioned in the center of the array 90, ten 880 nm diodes 188 are evenly positioned about the circumference of a circle of about 10.5 mm radius from the center of the array, and five 660 nm diodes 166 and five 950 nm diodes 195 are alternately positioned and evenly spaced about the circumference of a circle of about 17 mm radius from the center of the array, such that a radial line from the center of the array to each 660 nm or 950 nm diode, 166, 195 respectively, bisects the arc between two of the 880 nm diodes 188.

Another alternative embodiment of the cluster probe 60 of the present invention, shown in FIG. 8, comprises an array 100 of ten 660 nm superluminous diodes 166, one 820 nm laser diode 182, ten 880 nm superluminous or laser diodes 188, and ten 950 nm superluminous diodes 195. The diodes are arranged in a planar array such that the single 820 nm diode 182 is positioned in the center of the array, ten 880 nm diodes 188 are evenly positioned about the circumference of a circle of about 9.5 mm radius from the center of the array, ten 660 nm diodes 166 are evenly positioned about the circumference of a circle of about 18 mm radius from the center of the array such that a radial line from the center of the array to each 660 nm diode 166 bisects the arc between two of the 880 nm diodes 188, and ten 950 nm diodes 195 are evenly positioned about the circumference of a circle of 27 mm radius from the center of the array, such that a radial line from the center of the array to each 950 nm diode 195 passes through the center of one of the 880 nm diodes 188.

B. Theory of Operation

Figure 9:
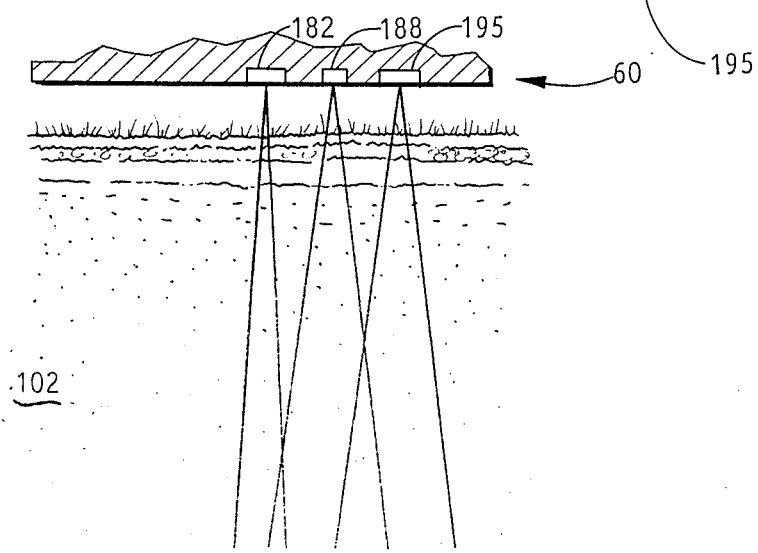
FIG. 9 is a simplified schematic view of the radiation beams of three diodes as used in the present invention impinging on a treatment tissue target.

The diodes within the array of each embodiment are closely arranged such that although the radiation they produce is emitted in a narrow beam, their beams overlap a short distance away from the surface of the cluster probe 60. Thus, as can be seen in FIG. 9, two or more wavelengths of radiation from the array 60 simultaneously pass through some point in the tissue 100 being stimulated. In FIG. 9, the divergence of each radiation beam is schematically shown for three radiation sources 182, 188 and 195 assumed to line along a single line. Radiation source 182 is assumed to have a beam divergence of six degrees, while radiation sources 188 and 195 are assumed to have beam divergence of 15 degrees. No other optical effects such as reflection, refraction or scattering are assumed. FIG. 9 shows that the beams will begin to overlap after they have traveled a few centimeters from the face of the cluster array 60. Obviously, overlap occurs even sooner when the diodes are more closely spaced.

When tissue is stimulated with these arrays of radiation sources, a cumulative, and sometimes synergistic, effect is believed to occur, which is not seen when a single wavelength is used. It has been proposed that this effect is due, in part, to the "mixing" of photons of different wavelengths which results in three types of "two-photon events". In the first type, two different adjacent molecules are excited by different wavelength photons. In the second type, two different parts of the same molecule are excited by different wavelength photons. Both of these types of events produce excited states that would not be possible if the same molecules were stimulated with photons of only one wavelength. These "new" excited states may also make the molecule(s) involved more susceptible to certain types of decay, dissipation and reaction with each other or other unexcited molecules.

In the third type of two-photon event, a single electron is simultaneously excited by two coinciding photons of different wavelengths. The high density of photons produced by devices of small emitting surface area of the present invention enhances the probability of this type of two-photon event occurring. Assuming that all of the simultaneously-presented energy is absorbed by an electron, the resultant quantum of energy delivered by two photons is equivalent to that of a photon of a much smaller wavelength. For example, for an 880 nm photon:

$$E_{880} = \frac{h \times c}{880 \text{ nm}}.$$

For an 820 nm photon:

$$E_{820} = \frac{h \times c}{820 \text{ nm}}.$$

Since the effective energy of both photons will be the sum of $E_{880}$ and $E_{820}$:

$$E_{effective} = E_{880} + E_{820} = \frac{h \times c}{\text{effective wavelength}}.$$

The effective wavelength is about one-half of the average of the two original wavelengths or, in this example, approximately 425 nm. In effect, the target molecule is stimulated as if it had been hit with a single 425 nm photon.

Figure 1:
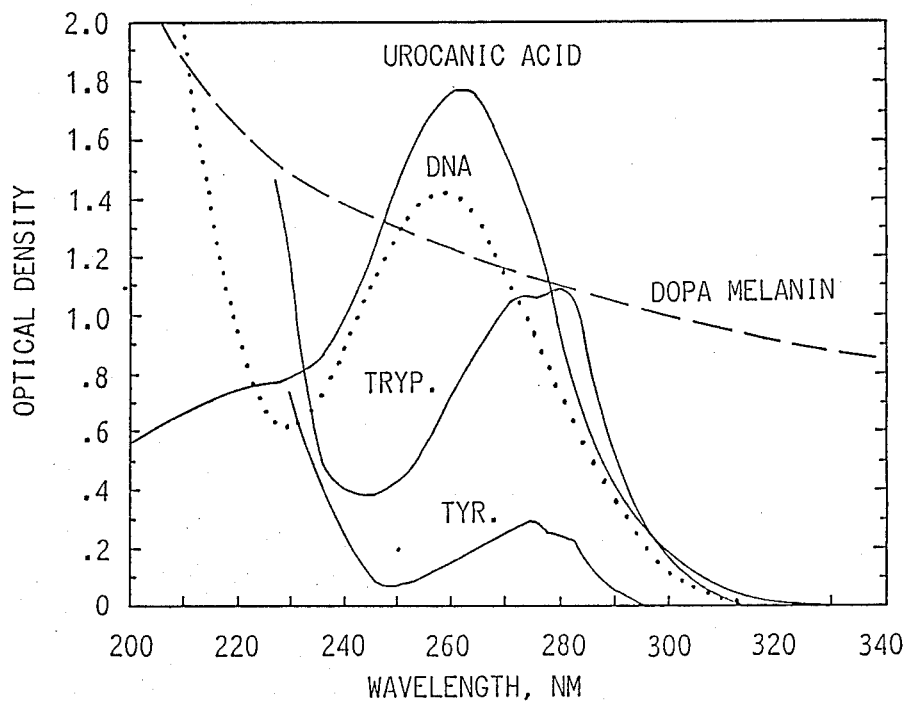
FIG. 1 is a graph summarizing the ultraviolet absorption spectra of major epidermal chromophores: DOPA-melanin, 1.5 mg% in H20; urocanic acid, $10^{-4}$M in H$_2$O; calf thymus DNA, 10 mg% in H$_2$O (pH 4.5); tryptophan $2\times10^{-4}$M (pH 7); tyrosine, $2\times10^{-4}$(pH 7). [From Pratesi and Sacchi, Eds., *Lasers in Photomedicine and Photobiology*, p. 165 (Springer 1980)].
Figure 2:
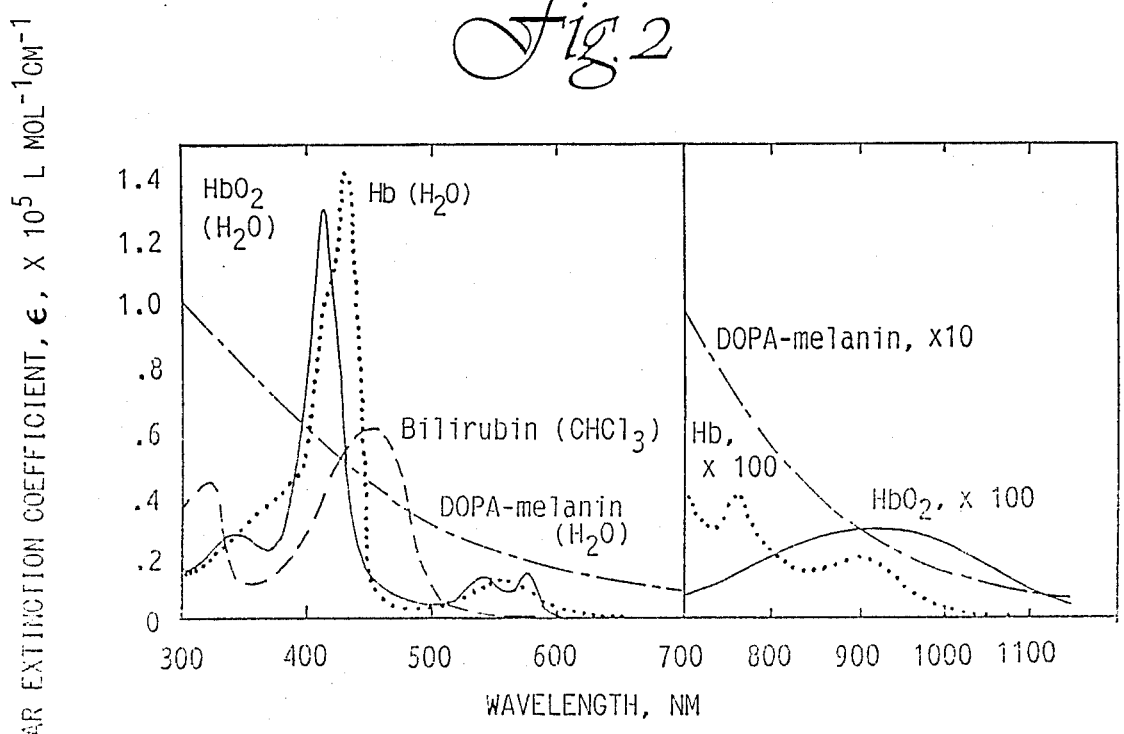
FIG. 2 is a graph summarizing the visible light absorption spectra of major human skin pigments. Parentheses indicate solvents used. [From Pratesi and Sacchi., *Lasers in Photomedicine and Photobiology*, p. 172 (Springer 1980)].
Figure 3:
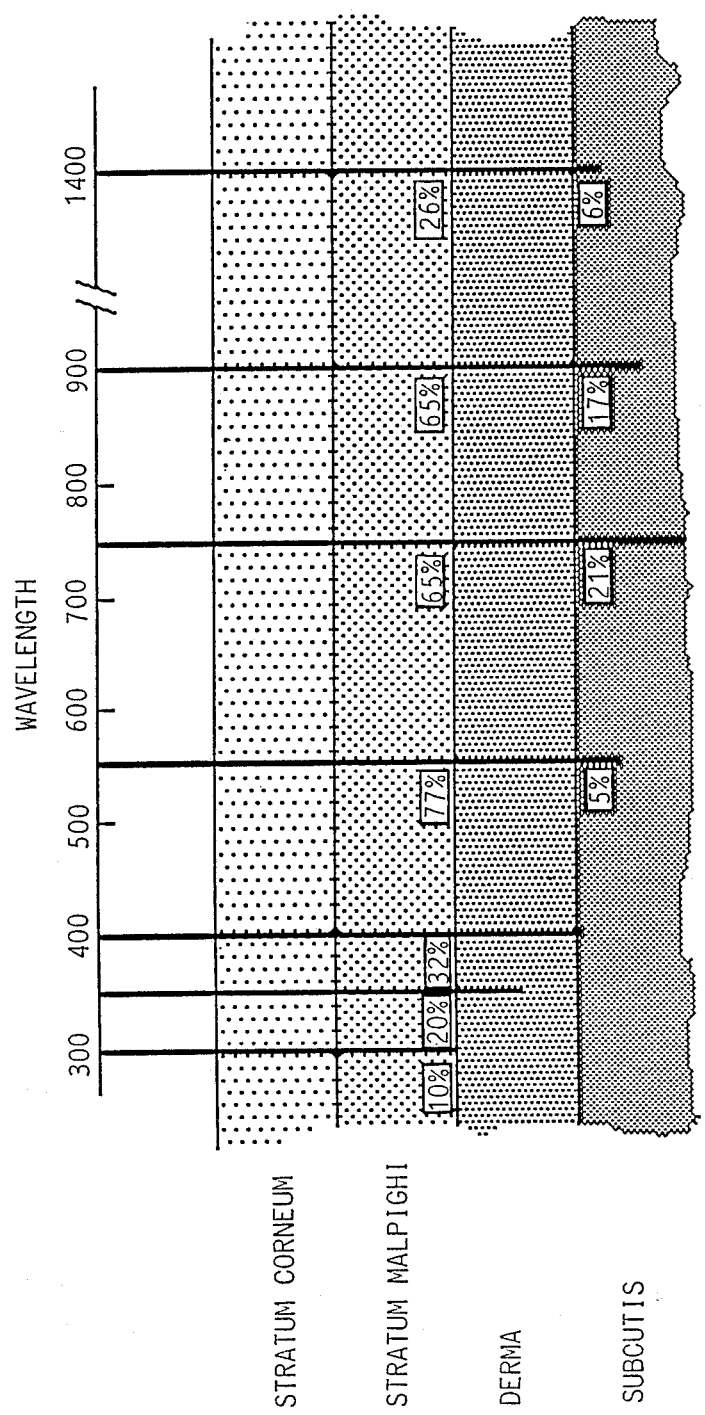
FIG. 3 is a pictorial and graphic representation of the relative penetration of various radiation wavelengths into human skin. [From D. Slimey and M. Wolbarsht, *Safety With Lasers and Other Optical Sources* (1980)].

The third type of two-photon even is especially significant because 425 nm is a wavelength that would normally be absorbed by skin pigments and would not penetrate very deeply into the skin. By stimulating the tissue with photons at 880 nm and 820 nm the screening effect of the skin is avoided. In certain preferred and alternative embodiments diodes of four wavelengths are used, thus creating ten different two-wavelength combinations, resulting in ten effective wavelengths during the third type of two-photon event. The effective wavelengths range from 330 nm to 475 nm which approximately corresponds to the range of highest absorption by skin pigments as shown in FIG. 2.

As noted above, an array of radiation sources as used in the present invention may be comprised of laser, superluminous and similar light-emitting diodes. These types of diodes are all substantially monochromatic non-gaseous radiation sources. Continuous wave diodes are preferable, because they have a higher average available power than pulsed diodes. Appropriate diodes are available from several suppliers at wavelengths of 650 nm, 660 nm, 680 nm, 750 nm, 780 nm, 800 nm, 810 nm, 820 nm, 830 nm, 840 nm, 850 nm, 860 nm, 870 nm, 880 nm, 900 nm, 904 nm, 1100 nm, 1300 nm and 1500 nm. These radiation sources are "substantially monochromatic," as that term is used throughout this specification and the appended claims, in that, in addition to emitting light or radiation at substantially one "main" wavelength, they also emit a significantly smaller amount of radiation at other wavelengths which are close, but not identical, to the "main" wavelength. A laser diode will emit at a "main" wavelength and a few peripheral wavelengths (corresponding to multiple resonances or off-axis modes) characterized by distinct narrow spikes in its wavelength spectrum. A superluminous or other light-emitting diodes will emit at a "main" wavelength that is at the peak of a somewhat broader continuous band of wavelengths in a wavelength spectrum. By convention, the "main" wavelength is used to identify the diode (e.g., a "800 nm diode" will emit at a "main" wavelength of 800 nm and at some other peripheral wavelengths characteristic of the material from which the diode is made). It should be noted that the number of combinations of two wavelengths leading to possible two-photon events is increased dramatically by the existence of peripheral wavelengths associated with the "main" wavelength of each type of diode. The slight variations in wavelength can lead to virtually hundreds of two-wavelength combinations and, as a result, hundred of effective wavelengths in the visible and ultraviolet spectra.

The present invention has as one objective the delivery of significant amounts of low-power radiation to deeper tissues. For this reason, the radiation sources, while low-powered, are relatively tightly-clustered. For the arrays shown in FIGS. 6–8, the average power density at the plane of the array is in the range from about 10 mW/cm$^2$ to about 40 mW/cm$^2$. Due to beam divergence, absorption, reflection, refraction, scattering and other similar effects, the average power density decreases with distance from the plane of the array either through air or into tissue. It should be noted, however, that due to the small radiation surface areas of some laser diodes, certain small areas near the plane of the array or at the surface of the treated tissue (when the cluster probe 60 is placed immediately adjacent the tissue) may have a power density of at least 120 mW/cm$^2$. Should it be found that higher energy densities yield enhanced biostimulative effects, without undesirable side effects, even higher powered diodes and/or somewhat more densely clustered diodes can be utilized. Of course, the energy delivered to a given area of tissue is also a function of time of exposure. Accordingly, it is also useful to speak of an energy density provided per unit area, defined as the power density multiplied by the exposure time. By this formula, a sixty second exposure of tissue with a minimum power density of 120 mW/cm$^2$ (which might be found to be a minimum exposure for some significant therapeutic result) could be described as of minimum treatment energy density of 7.2 Joules/cm$^2$.

In the preferred and alternative embodiments of present invention, the radiation sources can be modulated in pulses of different frequencies ranging from 2.28 Hz to 400 kHz, including 2.28 Hz, 4.56 Hz, 9.12 Hz, 16 Hz, 18.24 Hz, 36.48 Hz, 73 Hz, 146 Hz, 292 Hz, 700 Hz, 1000 Hz, 5 kHz and 300 kHz. This is done by means of the oscillator frequency control 47 mentioned above. Other frequencies could obviously be selected. As mentioned above, the beam oscillator 45 and its frequency control 47 can also provide pulse duration modulation for continuous wave radiation sources. Thus, for the same frequency a higher average power can be obtained according to the formula: P (average) = P (peak) × Pulse duration × Frequency.

2. Method of Treatment

The present invention also includes a method for treatment of tissue. The method involves exposing the tissue to a plurality of radiation sources of different wavelengths. More generally, the method of treatment of the present invention involves the simultaneous exposure of the tissue to at least three different wavelengths of radiation. Any embodiment of the device of the present invention, including but not limited to those previously described, can be used to perform this method of treatment. The array of radiation sources is preferably placed directly adjacent to or on the skin such that the plane of the radiation sources is close to or comes in contact with the outermost layer of skin. Because oils and other substances on the surface of the skin may cause absorption, refraction, reflection and/or diffraction of some wavelengths of radiation and thereby decrease radiation penetration, for effectiveness these should be removed before treatment.

Devices of the present invention have been used to treat various conditions in clinical settings. The results of those clinical applications as reported by several medical doctors and physiotherapists in the United Kingdom are summarized in the following examples.

EXAMPLE 1

A patient had a thirteen year history of extreme pain in the right big toe after engaging in sports activities. Upon examination, the patient was found to have a congenital Hallux Valgus or chronic "bunion". The sore toe was treated with a multi-diode biostimulation device of the present invention (660 nm, 820 nm, 880 nm, 950 nm) for a period of ten minutes. The patient experienced immediate relief of all pain and was able to engage in sports activities the day after treatment.

EXAMPLE 2

A patient experienced post plaster pain for two weeks following an operation for Hallux Valgus on the left foot. Examination revealed pitting edema of the forefoot, slight swelling of the ankle and limited movement of the foot. The patient was treated daily for five minutes with a multi-diode biostimulation device of the present invention (660 nm, 820 nm, 880 nm, 950 nm). Treatment continued for five days. Swelling decreased after each treatment. After the third treatment, the foot was pain free, but still slightly swollen. Upon completion of treatment, all symptoms had been relieved.

EXAMPLE 3

A 24 year-old patient experienced pain after surgery to repair a ruptured left anterior cruciate ligament. The patient was treated twice daily with a multi-diode biostimulation device of the present invention (660 nm, 820 nm, 880 nm, 950 nm) for a period of 4 minutes, 30 seconds. After treatment, the patient was pain free and showed signs of good tissue repair.

EXAMPLE 4

A 38 year-old patient had experienced chronic fibrositis in the neck for 18 years. The patient was treated daily for two days with a 21 diode biostimulation device of the present invention (660 nm, 820 nm, 880 nm, 950 nm) for a period of 4 minutes, 30 seconds. Each treatment was followed by treatment by treatment with a 15 mW 850 nm single diode probe for two minutes. After treatment, the patient experienced 98% pain relief.

EXAMPLE 5

A 35 year-old patient had experienced muscle spasms in the lower back. The patient was treated twice in a single day with a multi-diode biostimulation device of the present invention (660 nm, 820 nm, 880 nm, 950 nm)

for a period of 4 minutes, 30 seconds. After treatment, the patient experienced total pain relief.

EXAMPLE 6

A 33 year-old patient had experienced pain in the head of his fibula secondary to a knee injury in which the patient sustained a torn medial meniscus and ruptured anterior cruciate. The meniscus had been removed. The pain radiated down the leg and was associated with limitation of knee flexion. The patient was treated six times with a 660 nm single diode probe for a period of 4 minutes followed by treatment with a multi-diode biostimulation device of the present invention (660 nm, 820 nm, 880 nm, 950 nm) for a period of 2 minutes. Laser treatment was used in conjunction with mobilizations. After treatment, the patient experienced relief of virtually all pain and regained full range of knee flexion.

EXAMPLE 7

A 21 year-old patient had experienced an inflamed gleuteal bursa. The patient was treated three times with a 31 diode biostimulation device of the present invention (660 nm, 820 nm, 880 nm, 950 nm). After treatment, the patient showed no further pain and no reoccurrence.

EXAMPLE 8

A 35 year-old patient had experienced a non-healing skin ulcer for 3 years following a motorcycle accident. The patient was treated 10 times with a multi-diode biostimulation device of the present invention (660 nm, 820 nm, 880 nm, 950 nm). After treatment, the tissue showed increased granulation (++) and the ulcer had decreased in size and looked healthier.

EXAMPLE 9

A 70 year-old patient had experienced a diabetic ulcer following an above-knee amputation. The lateral third of the ulcer was treated with a 830 nm single diode probe and a multi-diode biostimulation device of the present invention (660 nm, 820 nm, 880 nm, 950 nm) for a period of 90 seconds each. After treatment, increased healing, granulation and de-sloughing were observed.

Preliminary indications are that the method and apparatus of the invention may be used widely for therapeutic purposes, for example, to treat inflammations, wounds, burns, chronic ulcerations including diabetic ulcers, deficient circulation, pain, nerve degeneration, eczema, shingles, infection, scars, acne, bone fractures, muscle and ligament injuries, arthritis, osteo-arthritis, rheumatoidal arthritis, skin grafts, gingival irritation, oral ulcers, dental pain and swelling, cellulitis, stretch marks, skin tone, alopecia areata, trigeminal neuralgia, herpes, zosten, sciatica, cervical erosions and other conditions.

From the foregoing, it will be obvious to those skilled in the art that various modifications in the above-described method and apparatus can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A device for biostimulation of tissue comprising:
   an array of substantially monochromatic radiation sources, said array comprising:
   at least one such radiation source providing a first wavelength less than 830 nm;
   at least one such radiation source providing a second wavelength greater than or equal to 830 nm and less than 900 nm; and
   at least one such radiation source providing a third wavelength greater than or equal to 900 nm;
   said radiation sources being arranged such that at least two radiation wavelengths among said first, second and third wavelengths simultaneously pass directly or indirectly through a single point located within said tissue.

2. The device for biostimulation of tissue of claim 1 wherein said radiation sources are selected from the group consisting of superluminous diodes and laser diodes.

3. The device for biostimulation of tissue of claim 2 wherein:
   said first wavelength is selected from the group consisting of 650 nm, 660 nm, 680 nm, 750 nm, 780 nm, 800 nm, 810 nm and 820 nm;
   said second wavelength is selected from the group consisting of 830 nm, 840 nm, 850 nm, 860 nm, 870 nm, and 880 nm; and
   said third wavelength is selected from the group consisting of 900 nm, 904 nm, 950 nm, 1100 nm, 1300 nm and 1500 nm.

4. The device for biostimulation of tissue of claim 2 wherein said array comprises:
   five 660 nm superluminous diodes;
   one 820 nm laser diode;
   ten 880 nm superluminous or laser diodes; and
   five 950 nm superluminous diodes.

5. The device for biostimulation of tissue of claim 4 wherein:
   said 820 nm diode is positioned in the center of said array;
   said 880 nm diodes are evenly positioned about the circumference of a circle of 10.5 mm radius from the center of said array; and
   said 660 nm diodes and 950 nm diodes are alternately positioned and evenly spaced about the circumference of a circle of 17 mm radius from the center of said array such that a radial line from the center of said array to each of said 660 nm of 950 nm diodes bisects the arc between two of said 880 nm diodes.

6. The device for biostimulation of tissue of claim 4 wherein:
   said 820 nm diode is positioned in the center of said array;
   fives of said 880 nm diodes are evenly positioned about the circumference of a circle of 10.5 mm radius from the center of said array;
   said 660 nm diodes are evenly positioned about the circumference of a circle of 17 mm radius from the center of said array such that a radial line from the center of said array to each of said 660 nm diodes bisects the arc between two of said 880 nm diodes in said first set;
   said 950 nm diodes are evenly positioned about the circumference of a circle of 17 mm radius from the center of said array such that a radial line from the center of said array to each of said 950 nm diodes passes through the center of one of said 880 nm diodes in said first set; and the remaining five of said 880 nm diodes are evenly positioned about the circumference of a circle of 27 mm radius from the center of said array such that a radial line from the center of said array to each of said 880 nm diodes passes through the center of one of said 660 nm diodes.

7. The device for biostimulation of tissue of claim 2 wherein said array comprises:
ten 660 nm superluminous diodes;
one 820 nm laser diode;
ten 880 nm superluminous or laser diodes; and
ten 950 nm superluminous diodes.

8. The device for biostimulation of tissue of claim 7 wherein:
said 820 nm diode is positioned in the center of said array;
said 880 nm diodes are evenly positioned about the circumference of a circle of 9.5 mm radius from the center of said array;
said 660 nm diodes are evenly positioned about the circumference of a circle of 18 mm radius from the center of said array such that a radial line from the center of said array to each of said 660 nm diodes bisects the arc between two of said 880 nm diodes; and
said 950 nm diodes are evenly positioned about the circumference of a circle of 27 mm radius from the center of said array such that a radial line from the center of said array to each of said 950 nm diodes passes through the center of one of said 880 nm diodes.

9. The device for biostimulation of tissue of claim 1 wherein:
said first wavelength is selected from the group consisting of 660 nm and 820 nm;
said second wavelength is selected from the group consisting of 875 nm and 880 nm; and
said third wavelength is 950 nm.

10. The device for biostimulation of tissue of claim 9 wherein said radiation sources are modulated at pulse frequencies selected from within the range of 2.28 Hz to 400 kHz.

11. The device for biostimulation of tissue of claim 10 wherein said pulse frequencies are selected from the group consisting of 2.28 Hz, 4.56 Hz, 9.12 Hz, 16 Hz, 18.24 Hz, 36.48 Hz, 73 Hz, 146 Hz, 292 Hz, 700 Hz, 1000 Hz, 5 kHz and 300 kHz.

12. A device for biostimulation of tissue comprising:
an array of substantially monochromatic radiation sources, said array comprising:
at least one such radiation source providing a first wavelength less than 830 nm;
at least one such radiation source providing a second wavelength greater than or equal to 830 nm and less than 875 nm;
at least one such radiation source providing a third wavelength greater than or equal to 875 nm and less than 900 nm; and
at least one such radiation source providing a fourth wavelength greater than or equal to 900 nm;
said radiation sources being arranged such that at least two radiation wavelengths among said first, second, third and fourth wavelengths simultaneously pass directly or indirectly through a single point located within said tissue.

13. The device for biostimulation of tissue of claim 12 wherein said radiation sources are selected from the group consisting of superluminous diodes and laser diodes.

14. The device for biostimulation of tissue of claim 13 wherein:
said first wavelength is selected from the group consisting of 650 nm, 660 nm, 680 nm, 750 nm, 780 nm, 800 nm, 810 nm and 820 nm;
said second wavelength is selected from the group consisting of 830 nm, 840 nm, 850 nm, 860 nm and 870 nm;
said third wavelength is 880 nm; and
said fourth wavelength is selected from the group consisting of 900 nm, 904 nm, 950 nm, 1100 nm, 1300 nm and 1500 nm.

15. A device for biostimulation of tissue comprising:
an array of substantially monochromatic light-emitting diodes, said array comprising:
at least one diode providing a first wavelength less than 800 nm; and
at least one diode providing a second wavelength greater than or equal to 800 nm;
said diodes being arranged such that radiation of said first and second wavelengths simultaneously passes directly or indirectly through a single point located within said tissue.

16. The device for biostimulation of tissue of claim 15 wherein:
said first wavelength is selected from the group consisting of 650 nm, 660 nm, 680 nm, 750 nm and 780 nm; and
said second wavelength is selected from the group consisting of 800 nm, 810 nm, 820 nm, 830 nm, 840 nm, 850 nm, 860 nm, 870 nm, 900 nm, 904 nm, 950 nm, 1100 nm, 1300 nm and 1500 nm.

17. A device for biostimulation of tissue comprising:
an array of substantially monochromatic low-power, light-emitting diodes, said diodes being modulated by frequency and pulse duration, individually having continuous power of 5 to 500 milliwatts, being arranged to emit light from essentially a single plane and together emitting an average power density at said plane of at least 10 mW/cm$^2$.

18. A device for biostimulation of tissue comprising:
an array of substantially monochromatic low-power, light-emitting diodes, said diodes being modulated by frequency and pulse duration, individually having continuous power of 5 to 500 milliwatts and being arranged so as to provide a power density of at least 120 mW/cm$^2$ at a point on the surface of said tissue.

19. A device for biostimulation of tissue comprising:
an array of substantially monochromatic non-gaseous continuous wave low-power radiation sources, said radiation sources being modulated by frequency and pulse duration, individually having continuous power of 5 to 500 milliwatts, being arranged to emit light from essentially a single plane and emitting an average power density at said plane of at least 10 mW/cm$^2$.

20. A device for biostimulation of tissue comprising:
an array of substantially monochromatic non-gaseous continuous wave low-power radiation sources, said radiation sources being modulated by frequency and pulse duration, individually having continuous power of 5 to 500 milliwatts and being arranged so as to provide a power density of at least 120 mW/cm² at a point on the surface of said tissue.

21. A method for treatment of tissue comprising:
providing an array of substantially monochromatic radiation sources, said array comprising:
at least one such radiation source providing a first wavelength less than 830 nm;
at least one such radiation source providing a second wavelength greater than or equal to 830 nm and less than 900 nm; and
at least one such radiation source providing a third wavelength greater than or equal to 900 nm;
said radiation sources being arranged such that when activated at least two radiation wavelengths among said first, second and third wavelengths simultaneously pass directly or indirectly through a single point located within said tissue; and
exposing said tissue to a radiation beam produced by said array.

22. The method for treatment of tissue of claim 21 further comprising selecting said radiation sources from the group consisting of superluminous diodes and laser diodes.

23. The method for treatment of tissue of claim 22 further comprising selecting the following radiation sources to form an array;
five 660 nm superluminous diodes;
one 820 nm laser diode;
ten 880 nm superluminous or laser diodes;
and five 950 nm superluminous diodes.

24. The method for treatment of tissue of claim 23 further comprising:
positioning said 820 nm diode in the center of said array;
positioning said 880 nm diodes evenly about the circumference of a circle of 10.5 mm radius from the center of said array; and
positioning said 660 nm diodes and 950 nm diodes alternately and evenly spaced about the circumference of a circle of 17 mm radius from the center of said array such that a radial line from the center of said array to each of said 660 nm or 950 nm diode bisects the arc between two of said 880 nm diodes.

25. The method for treatment of tissue of claim 23 further comprising:
positioning said 820 nm diode in the center of said array;
positioning five of said 880 nm diodes evenly about the circumference of a circle of 9.5 mm radius from the center of said array to form a first set;
positioning said 660 nm diodes evenly about the circumference of a circle of 18 mm radius from the center of said array such that a radial line from the center of said array to each of said 660 nm diodes bisects the arc between two of said 880 nm diodes in said first set;
positioning said 950 nm diodes evenly about the circumference of a circle of 27 mm radius from the center of said array such that a radial line from the center of said array to each of said 950 nm diodes passes through the center of one of said 880 nm diodes in said first set; and
positioning the remaining five of said 880 nm diodes evenly about the circumference of a circle of 27 mm radius from the center of said array such that a radial line from the center of said array to each of said remaining five 880 nm diodes passes through the center of one of said 660 nm diodes.

26. The method for treatment of tissue of claim 22 further comprising selecting the following radiation sources to form an array:
ten 660 nm superluminous diodes;
one 880 nm superluminous or laser diodes; and
ten 950 nm superluminous diodes.

27. The method for treatment of tissue of claim 26 further comprising:
positioning said 820 nm diode in the center of said array;
positioning said 880 nm diodes evenly about the circumference of a circle of 9.5 mm radius from the center of said array;
positioning said 660 nm diodes evenly about the circumference of a circle of 18 mm radius from the center of said array such that a radial line from the center of said array to each of said 660 nm diodes bisects the arc between two of said 880 nm diodes; and
positioning said 950 nm diodes evenly about the circumference of a circle of 27 mm radius from the center of said array such that a radial line from the center of said array to each of said 950 nm diodes passes through the center of one of said 880 nm diodes.

28. A method for treatment of tissue comprising:
removing from the surface of said tissue absorbing, refracting, reflecting or diffracting substances;
providing an array of substantially monochromatic radiation sources, said array comprising:
at least one such radiation source providing a first wavelength less than 830 nm;
at least one such radiation source providing a second wavelength greater than or equal to 830 nm and less than 900 nm; and
at least one such radiation source providing a third wavelength greater than or equal to 900 nm;
said radiation sources being arranged such that when activated at least two radiation wavelengths among said first, second and third wavelengths simultaneously pass directly or indirectly through a single point located within said tissue; and
exposing said tissue to a radiation beam produced by said array.

29. The method for treatment of tissue of claim 28 further comprising selecting said radiation sources from the group consisting of light-emitting diodes, superluminous diodes and laser diodes.

30. A method for treatment of tissue comprising:
exposing said tissue to a radiation source providing a first wavelength less than 830 nm;
simultaneously exposing said tissue to a radiation source providing a second wavelength greater than or equal to 830 nm and less than 900 nm;
simultaneously exposing said tissue to a radiation source providing a third wavelength greater than or equal to 900 nm; and
arranging said radiation sources such that at least two radiation wavelengths among said first, second and third wavelengths simultaneously pass directly or indirectly through a single point located within said tissue.

31. The method for treatment of tissue of claim 30 further comprising selecting said radiation sources from the group consisting of superluminous diodes and laser diodes.

32. A method for treatment of tissue comprising:
measuring the electrical conductivity of said tissue to locate an area of conductivity greater than a preselected threshold minimum conductivity, and
providing an array of substantially monochromatic radiation sources, said array comprising:
at least one such radiation source providing a first wavelength less than 830 nm;
at least one such radiation source providing a second wavelength greater than or equal to 830 nm and less than 900 nm; and
at least one such radiation source providing a third wavelength greater than or equal to 900 nm;
arranging said radiation sources such that at least two radiation wavelengths among said first, second and third wavelengths simultaneously pass directly or indirectly through a single point located within said tissue; and
exposing said area of conductivity to a radiation beam produced by said array.

33. The method for treatment of tissue of claim 32 further comprising selecting said radiation sources from the group consisting of superluminous diodes and laser diodes.

34. A method for treatment of tissue comprising:
exposing said tissue to a first radiation beam of substantially monochromatic radiation of a wavelength within one wavelength range selected from the group consisting of the wavelength range 300-830 nm, the wavelength range 830-900 nm and the wavelength range 900-1500 nm;
thereafter exposing said tissue to a second radiation beam of substantially monochromatic radiation of a wavelength within one wavelength range not previously selected from said group; and
thereafter exposing said tissue to a third radiation beam of substantially monochromatic radiation of a wavelength within the remaining wavelength range not previously selected from said group.

35. The method for treatment of tissue of claim 34 further comprising selecting said radiation sources from the group consisting of superluminous diodes and laser diodes.

36. A system for biostimulation of tissue comprising:
a biostimulation device comprising:
an array of substantially monochromatic radiation sources, said array comprising:
at least one such radiation source providing a first wavelength less than 830 nm;
at least one such radiation source providing a second wavelength greater than or equal to 830 nm and less than 900 nm; and
at least one such radiation source providing a third wavelength greater than or equal to 900 nm;
said radiation sources being arranged such that at least two radiation wavelengths among said first, second and third wavelengths simultaneously pass directly or indirectly through a single point located within said tissue; and
means in communication with said array for providing power to said radiation sources such that each of said radiation sources emits radiation at its characteristic wavelength.

37. The system for biostimulation of tissue of claim 36 wherein said system further comprises:
means in communication with said power-providing means for modulating the output of said sources with pulses and varying the modulation pulse frequency of said radiation sources.

38. The system for biostimulation of tissue of claim 36 wherein said system further comprises:
means in communication with said power-providing means for varying the pulse duration of said radiation sources.

39. The system for biostimulation of tissue of claim 36 wherein said system further comprises:
means in communication with said power-providing means for timing the period that power is provided to said radiation sources.

40. The system for biostimulation of tissue of claim 36 wherein said system further comprises:
means in communication with said power-providing means for measuring the electrical conductivity of said tissue.

41. The system for biostimulation of tissue of claim 36 wherein said system further comprises:
means in communication with said array for measuring the optical power emitted by said radiation sources.

42. The system for biostimulation of tissue of claim 36 wherein said system further comprises:
means in communication with said control panel for detecting radiation from said radiation sources; and
indicator means connected to said detecting means for indicating that radiation is being emitted from said radiation sources.

43. A system for biostimulation of tissue comprising:
a biostimulation probe comprising:
an array of substantially monochromatic radiation sources, said array comprising:
at least one such radiation source providing a first wavelength less than 830 nm;
at least one such radiation source providing a second wavelength greater than or equal to 830 nm and less than 900 nm; and
at least one such radiation source providing a third wavelength greater than or equal to 900 nm;
said radiation sources being arranged such that at least two radiation wavelengths among said first, second and third wavelengths simultaneously pass directly or indirectly through a single point located within said tissue;
means in communication with said array for providing power to said radiation sources such that each of said radiation sources emits radiation at its characteristic wavelength;
means in communication with said power-providing means for modulating the pulse frequency of said radiation sources;
means in communication with said power-providing means for varying the pulse duration of said radiation sources;
means in communication with said power-providing means for timing the period that power is provided to said radiation sources;
means in communication with said array for measuring the electrical conductivity of said tissue;
means in communication with said power-providing means for measuring the optical power emitted by said radiation sources; and
means in communication with said control panel for detecting emissions from said radiation sources.

* * * * *